United States Patent [19]
Gorti

[11] Patent Number: 5,954,658
[45] Date of Patent: Sep. 21, 1999

[54] METHOD AND APPARATUS FOR MEASURING BLOOD FLOW AT PRECISE DEPTHS IN TISSUE AND SKIN

[76] Inventor: Sridhar Gorti, 12311 Pond Run Dr., #104, Woodbridge, Va. 22192

[21] Appl. No.: 09/045,329

[22] Filed: Mar. 20, 1998

Related U.S. Application Data

[60] Provisional application No. 60/041,336, Mar. 21, 1997.

[51] Int. Cl.[6] ............................................. A61B 5/026
[52] U.S. Cl. ................................... 600/504; 600/476
[58] Field of Search ................................. 600/504, 476, 600/465; 356/28; 128/633

[56] References Cited

U.S. PATENT DOCUMENTS

| | | | |
|---|---|---|---|
| 4,862,894 | 9/1989 | Fujii | 600/479 |
| 5,291,886 | 3/1994 | Katayama et al. | 128/633 |
| 5,339,817 | 8/1994 | Nilsson | 600/473 |
| 5,361,769 | 11/1994 | Nilsson | 600/504 |
| 5,833,612 | 11/1998 | Eckhouse et al. | 600/476 |
| 5,845,639 | 12/1998 | Hochman et al. | 600/476 |

*Primary Examiner*—William E. Kamm
*Assistant Examiner*—Ali M. Imam

[57] ABSTRACT

A non-invasive, non-traumatic technology for measuring continuously the blood flow and volume at precise depths within tissues is presented. The new methodology makes use of 1) a long-wavelength visible laser or semiconductor laser light delivered at a variable incidence angle for triangulating onto a specific region under investigation, 2) a lens system which magnifies the area illuminated by the laser light as it propagates within the tissue, 3) a translating optical fiber or a linear array of optical fibers that collect the back scattered photons emanating from the surface of the tissue along the expected trajectory of the laser light propagating within the tissue, 4) a photo diode or a photo multiplier, or a bank of photo diodes or photo multipliers that amplify and convert the back scattered photons into electrical signals, 5) a system for collectively or selectively monitoring both the static and dynamic properties of the back scattered photons, and 6) an algorithm or algorithms which determine not only the location, volume and velocities of blood flow at precise depths within the tissue, but may also determine the thickness as well as the elasticity of the tissues above the region(s) where blood flow first occurs. Furthermore, this newly developed technology can also provide a 2-dimensional map of the blood flow regions within tissues in terms of depth and blood flow characteristics.

7 Claims, 11 Drawing Sheets

Power spectra of the depolarized component of backscattered laser light emitted at the surface of the skin

The Method of Triangulation

METHOD AND APPARATUS FOR MEASURING BLOOD FLOW AT PRECISE DEPTHS IN TISSUE AND SKIN

CROSS REFERENCE TO RELATED APPLICATION

This application claims the benefit of U.S. Provisional Application Ser. No. 60/041,336 filed Mar. 21, 1997.

BACKGROUND OF THE INVENTION

1. Field of the Invention

This invention relates generally to medical instrumentation and more particularly to opto-electronic devices that non-invasively measure and determine the velocity and magnitude of blood flow within tissues as well as the thickness and dynamics (other than and/or unrelated to blood flow) of specific components of the tissue when it is comprised of distinct layers. Moreover, it also pertains to measurement instruments that possess the ability to determine the precise location of boundary regions between distinct layers of tissue, as well as triangulate onto the region(s) where initial fluid movement occurs.

2. Description of the Prior Art

Laser-Doppler methodology, as applied to the measurement of blood flow, was initially described by in an article entitled "In Vivo Evaluation of Microcirculation by Coherent Light Scattering", written by Stern, which appeared in Nature, Vol. 254, pages 56–58 in 1975. The basic principles of this methodology are that the frequency of the laser light back scattered or reflected by a laser illuminated tissue is Doppler broadened, due mostly in part to the motions of red blood cells. The extent to which the initial laser frequency is broadened as well as the light intensity within specific parts of the broadened frequency spectrum, both provide information regarding the relative motions and concentration of red blood cells within the tissue.

Utilizing these established methodologies which correlate laser-Doppler signals to red blood cell concentrations and motions within tissues, several commercially-available blood flow monitors that rely on laser/laser-diode and fiber optic technologies have been developed. The essential elements of these systems incorporating the laser-Doppler methodology are: a) a laser beam delivered directly onto a part of the tissue, usually by means of an optical "outlet" fiber where the laser light is unfocused and divergent; b) an optical element that receives a portion of any back scattered or reflected laser light from the illuminated tissue, also typically by means of an optical "pick-up" fiber placed in the vicinity of the outlet fiber ($\geq 100$ $\mu$m optical fiber center-center distance); c) an appropriate means for converting photon flux to electrical signals, and d) an algorithm that realistically represents the movement and approximate numbers of red blood cells within the tissue, as a function of time. A characteristic common to these first-generation blood flow monitoring systems is that they all use outlet and pick-up optical fibers that directly contact the tissue when delivering and accepting laser light normal to a surface of the skin being measured.

More recently, second generation blood flow monitors have incorporated new adaptations in the optics of the laser light delivery system and back scattered laser light detection technologies, which now allow for the measurement of blood flow over an area of a body part. In particular, U.S. Pat. No. 4,862,894 issued to Fuji on Sep. 5, 1989; U.S. Pat. No. 5,291,885 issued to Taniji, et al. on Mar. 8, 1994; U.S. Pat. No. 5,291,886 issued to Katayama, et al. on Mar. 8, 1994; and U.S. Pat. No. 5,339,817 issued to Nilsson on Aug. 23, 1994, all describe systems which permit the measurement of blood flow within a body part.

The optical modification taught by these systems is comprised of a laser light source that can be focused, to a point or a line source, and positioned at specific locations within an area of body by means of scanning optical mirrors. The total back scattered or reflected laser light Doppler or speckle signal from each independent location within an area of body is also collected by the same optical mirrors and partially reflected to a photodetecting system. The obtained electrical signals, in time, are then processed in a manner similar to the first generation blood flow monitors so as to represent the movement and approximate numbers of red blood cells at each specific location within an area of the body. Upon completion of one scanning location, the laser beam is repositioned to a new location, where the Doppler signal collection and analyses, in time, is once again performed. This process is repeated for the entire area of the body that is of interest. Concurrent with obtaining blood flow characteristics at each location within an area of body, a visible image of the area is also recorded by means of video imaging. Both the visible image and blood flow characteristics at each location are later superimposed to yield the approximate characteristics of blood flow for the area of the body. An additional feature of the new optical arrangement is that it is no longer in direct contact with the tissue. To its detriment, however, is that the delivery and acceptance of laser light is still essentially normal to the skin surface.

Regardless of which type of prior art optical arrangement one employs however, systems employing these prior art arrangements are inadequate in locating precisely the region within the skin where blood flow originates. In particular, of four main criteria established to determine the utility of systems to measure blood flow within the skin: 1) non-traumatic and non-invasive, 2) accurately follow blood flow, 3) sensitive to small changes, and 4) insensitive to blood flow from other parts of the tissue or tissues, all blood flow monitors described above fail to meet two of the most significant criteria. Specifically, they are insensitive to small changes and insensitive to blood flow from other parts of the tissue or tissues. Moreover, these laser Doppler systems also fail to yield other characteristics of the skin apart from blood flow. Consequently, a continuing need exists in the art for methods and apparatus which provide non-invasive blood flow and tissue information.

SUMMARY OF THE INVENTION

The present invention provides a method and apparatus for non-invasive in vivo measurement of blood flow characteristics at precise locations or regions within tissues that is also sensitive to small changes in blood perfusion. In addition to monitoring blood flow, the invention is also capable of determining other physical characteristics of the tissue, such as: the thickness of the tissue above the region(s) where blood flow was first observed to occur, and where applicable, the elasticity of that tissue. The invention is a non-contact, in vivo method that is based on the detailed observations of the scattered photons emitted at the surface of tissue as a highly collimated narrow laser beam or a focused laser light spot or line that is positioned on the surface of the tissue at a specific angle or variable angles. An optical receiving system focused on the measurement plane of the tissue collects and collimates light back scattered from not only the initial position of laser incidence, but also the light emitted at the surface of the tissue as the initially inserted laser beam propagates beneath the surface of the tissue and into deeper regions. A portion of the back scattered light is reflected into a video system to obtain a visible image. By means of a translating optical fiber probe or a fiber probe array, a photodetecting system partitions the remainder of the back scattered laser light collected by the optical receiving system. Each partition represents contiguous locations on the surface of the tissue from which the surface emitted back scattered laser light, along the propagating vector or trajectory of the initially inserted laser beam beneath the surface of the tissue, is collected. Thereby, each partition evidences the unique static and dynamic properties of light back scattered from different regions of the tissue through which the initially inserted laser light is traversing at different depths. The results of these measurements are subsequently output into readily usable and easily understandable forms.

In a particular use of the invention, specifically, where the invention is applied to measure the blood flow and other physical properties of the skin, appropriate analyses of both the static and dynamic properties of back scattered light from all contiguous optical fiber probe sampling positions enables the determination of the thickness of the stratum corneum and the epidermal region, the elasticity of the stratum corneum, the blood flow precisely at the epidermal/dermal boundary region, the general texture or shape of the boundary region, and the blood flow characteristics of tissue beneath the boundary region. The thickness of the layers of the skin is obtained by the method of triangulation which makes use of geometry, the refractive index of the tissue medium and the optical fiber position on the surface of the tissue from which the back scattered light is partitioned and monitored. The optical fiber position essentially signifies the depth of the region(s) from whence the initially inserted laser light is scattered back towards the surface of the tissue. The selection of the position used to calculate the depth of a specific region within the tissue will be determined either by the static or by both the static and dynamic properties of the scattered light observations from contiguous locations on the surface of the tissue. For such cases when the refractive index of the tissue medium is unknown, observations of the back scattered laser light emanating from the surface of the tissue need be performed for several laser light incidence angles prior to the exact determination of the depth of a specified region. In addition to thickness determinations, the invention makes use of correlation functions to analyze the dynamic properties of the back scattered laser light collected by optical fibers positioned in the vicinity of the initial laser light insertion point, in order to ascertain the elastic properties of the stratum corneum.

By the method of triangulation, the invention also determines the precise depth or location of the epidermal/dermal boundary region at which capillary blood flow occurs. That is, at a location or an optical fiber position far removed from the initial laser light insertion position, a maximum in the magnitude of the frequency shifted Doppler signal is observed when the optical fiber position and the initially inserted laser light propagating beneath the tissue triangulate onto the epidermal/dermal boundary region where capillary blood flow is known to occur. Appropriate signal processing method(s) can further determine capillary blood perfusion in the region by detailing not only the amplitude of the Doppler signal, but also the velocity of the red blood cell motion. Thus the invention is capable of real time scattered light signal collection and analyses for determining capillary blood perfusion, as well as the heart rate and quite possibly the respiration rate within tissues. Because of structural irregularities that exist within the epidermal/dermal boundary region, the determination of both the amplitude of the Doppler signal and the velocity of red blood cell motions is also necessary to triangulate onto the precise location of the boundary region when one or more apparent maximums in the magnitude of the frequency shifted Doppler signal are present. The number of maximums observed is dependent not only on the irregularity of the boundary region, but also the laser light incidence angle. By varying the laser light incidence angle and repeating the above measurements, as well as by performing the same series of measurements over an area of the skin and then mapping all information relating the depth and location of blood flow, the invention is thus also capable of generating an accurate 2-dimensional representation of the irregular structure of the epidermal/dermal boundary in terms of blood perfusion characteristics. The combined results of these measurements may also be displayed into readily usable and easily understandable forms.

DESCRIPTION OF THE DRAWING

A detailed description of the invention, its purposes and features described herein, will become more apparent when taken in conjunction with the accompanying drawing in which.

DETAILED DESCRIPTION OF THE INVENTION

Figure 1:
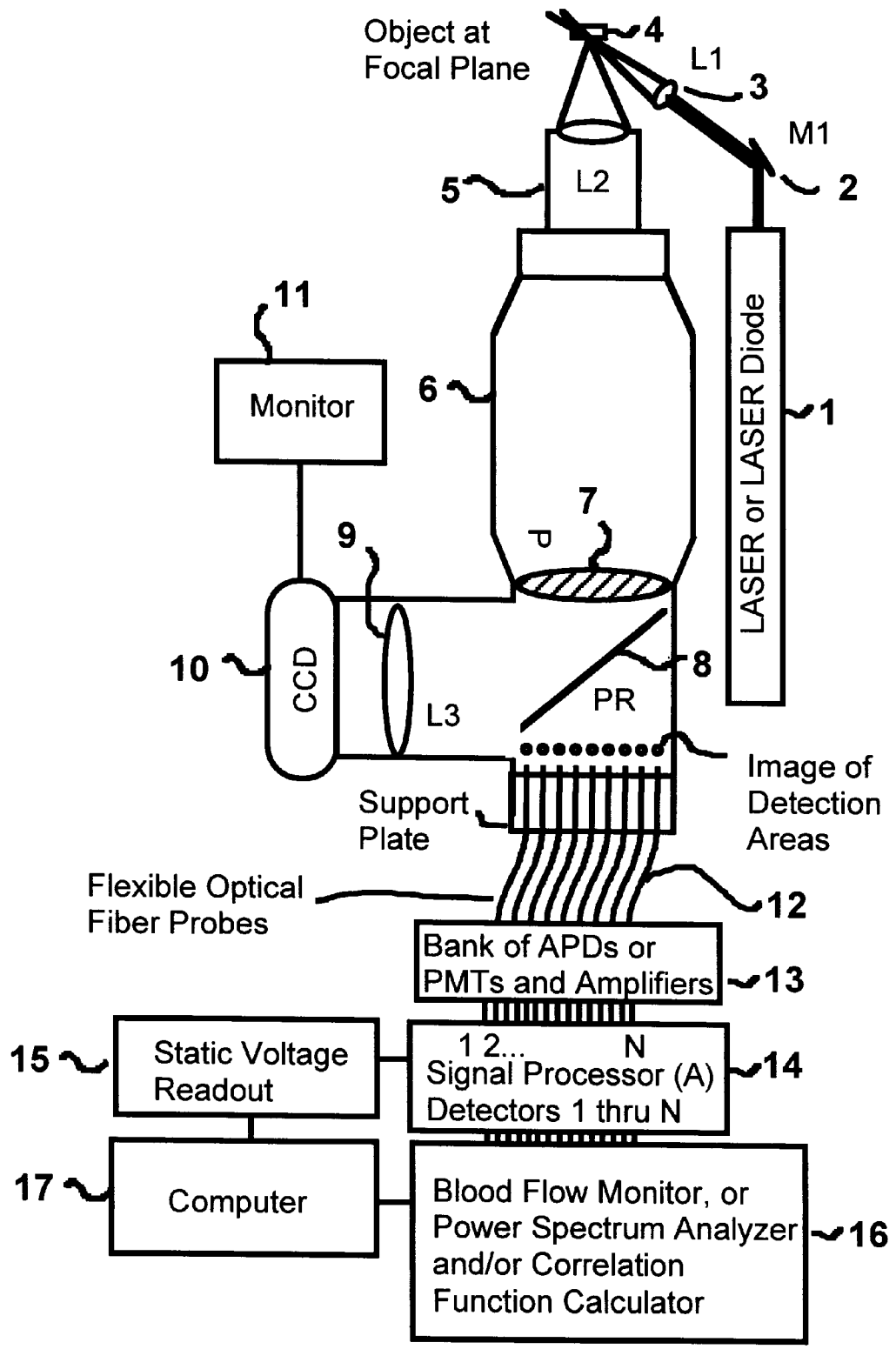
FIG. 1 is a simple schematic of an apparatus for measuring the capillary blood flow volume and velocities at an epidermal/dermal boundary region, a thickness of stratum corneum and epidermis, and stratum corneum elasticity according to the principles of the present invention.

The significant features or preferred embodiments of the invention, illustrated schematically in FIG. 1, that distinguishes itself from other types of blood flow monitors include: a) the delivery of a long-wavelength visible light emanating from a laser or semiconductor laser at a specific yet adjustable incidence angle, b) the collection optics which magnify that area of the tissue illuminated not only by the initially inserted laser light but also by laser light back scattered to the surface of the tissue as the initially inserted laser light propagates beneath the tissue's surface, c) the partitioning and contiguous sampling of photons emanating from the surface of the tissue within this area but along the expected trajectory of the propagating laser light by a translating optical fiber or an array of optical fibers, and d) the user or computer selectable algorithm(s) developed for the data analyses and presentation of the resulting measurements which determine blood flow characteristics at precise depths within the tissue, the thickness and the elasticity of the tissues above the region(s) where blood flow first occurs and/or 2-dimensional representation of the structure of the blood flow region(s) in terms of blood perfusion characteristics, or any combination thereof.

Figure 2:
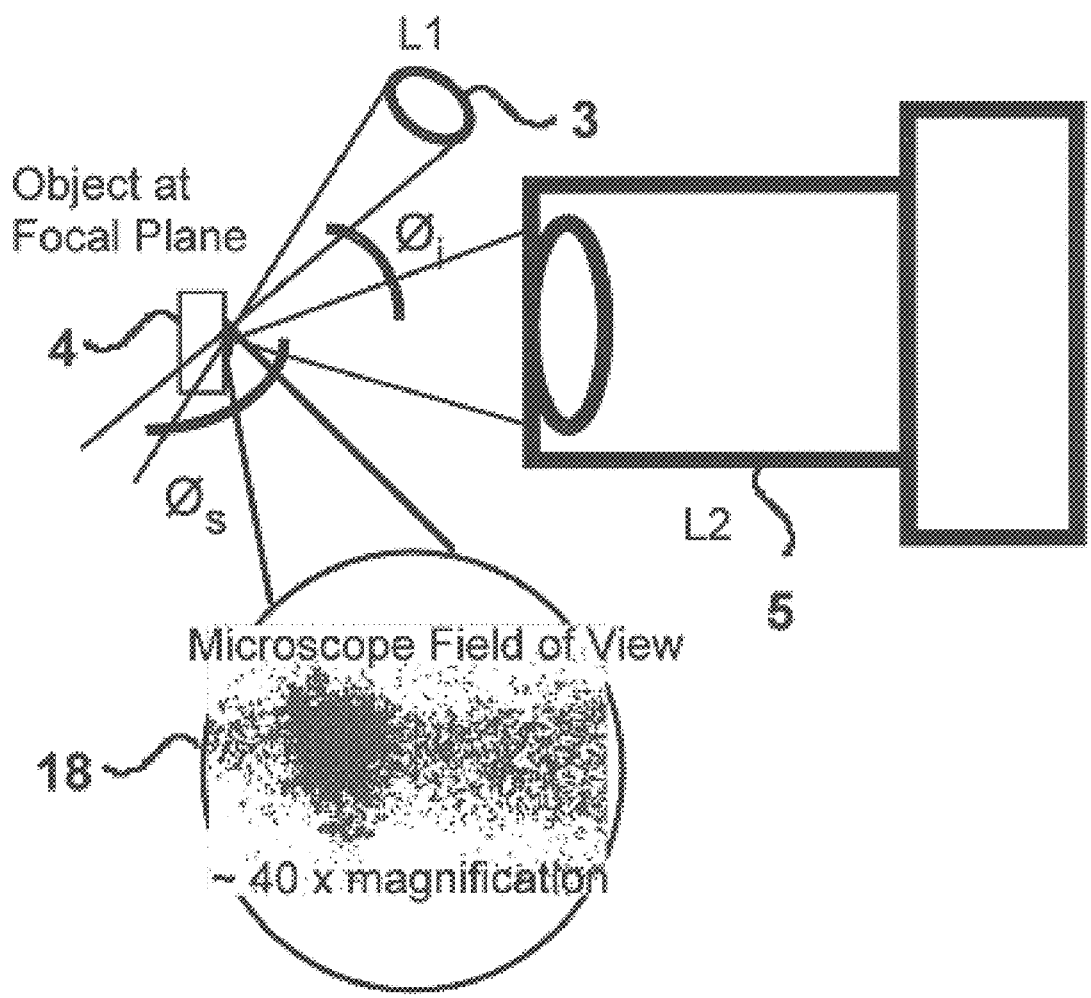
FIG. 2 depicts the essential geometry of laser light incidence and collection angles, as well as a desired sample position.
Figure 3:
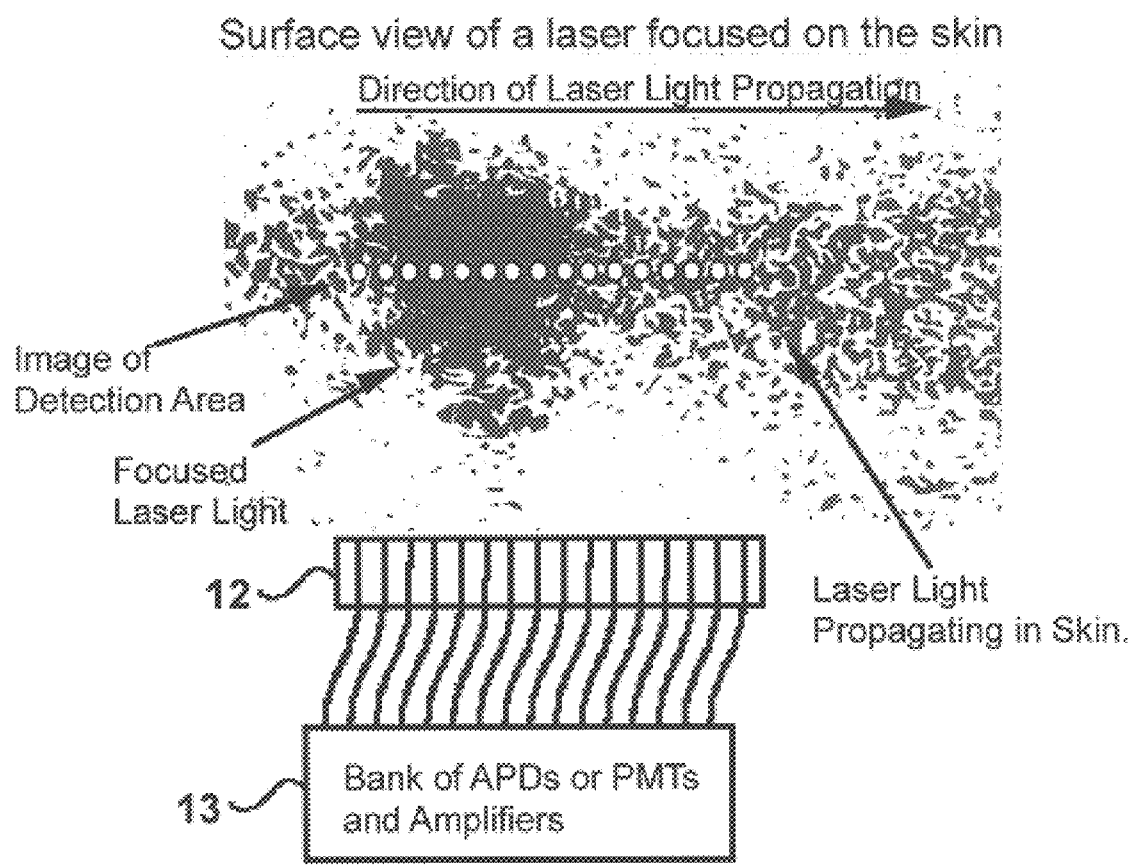
FIG. 3 shows the actual field of view (Top View) of the collection optics where a laser light focused on the surface of the skin is seen propagating within the skin.

We now describe in detail each significant aspect of the invention whose simplified schematic is diagrammed in FIG. 1. A vertically polarized laser beam emitted by a laser source 1 is reflected by a mirror 2 and passes through a lens 3. At this stage of the process, it is necessary that the diameter of the laser light focal point need be small, in the range of ~40 $\mu$m to ~100 $\mu$m, and the laser polarization be normal in orientation with respect to the back scattered light collection optics. As shown in FIG. 2, the focal point of the lens 3 is positioned on the surface an object 4 which is on a stage resting at the focal plane of the collection lens 5. That is, the focal point of the laser beam exiting the lens 3, the sample surface 4 and the focal point of the collection lens 5 are coincident on the same plane. FIG. 2 also illustrates the overall laser light incidence and back scattered laser light collection geometry of the system, as well as the positioning of the initially inserted laser beam within the field of view of the collection optics 5. The collection optics 5 may be commercially available compound microscope objectives whose magnification can range from 4x to 32x or greater if necessary, provided that the field of view be sufficently large to enable triangulation onto the required depth of tissues. All scattered light collected within this field of view is then collimated into a microscope body 6. The back scattered collumated light within the boby of the microscope 6 is passed through a polarizer 7 whose orientation can be adjusted to allow for polarized (∥) or depolarized (☐) scattered light sampling. A portion or most of the collumated light is reflected by a partial reflector 8 into the side port which contains a lens coupled to a reticle 9 that focuses the collected image 18, shown in FIG. 2 and FIG. 3, onto a CCD or televison camera 10. The image obtained by the camera 10 is forwarded to a monitor 11 which would then enable the user to properly align the focused laser beam and the collection optics 5 onto the object resting on a stage 4. Once optical alignment is satisfacory, the partial reflector 8 may be rotated out of position to allow for all back scattered collumated light to pass towards either a translating optical fiber probe or an arrray of optical fiber probes 12. FIG. 3 displays an image of both the laser light initially focused on the surface propagating into the deeper regions of a rats' foot skin, and the subsequent sampling of the back scattered laser light collected within the field of view of the microscope at contiguous locations on the surface of the object by either a translating optical fiber probe or an arrray of optical fiber probes 12. As also depicted in FIG. 3, only a portion (a partitioned region) or small area of the back scattered laser light collected within the field of view of the microscope is sampled by either a translating optical fiber probe or each individual optical "pick-up" fiber within the array 12, at any given time. The back scattered light sampled within a specific area is guided to an individual avalanche photo diode (APD) or photo multiplier tube (PMT), or a bank of APD's or PMT's 13 through each respective optical fiber. The photon flux sampled from within each area on the surface of the object is amplified and converted to an electrical signal that is delivered to a signal processor unit 14 and then treated in accordance with another aspect of the invention which provides user selectable algorithms.

Figure 4:
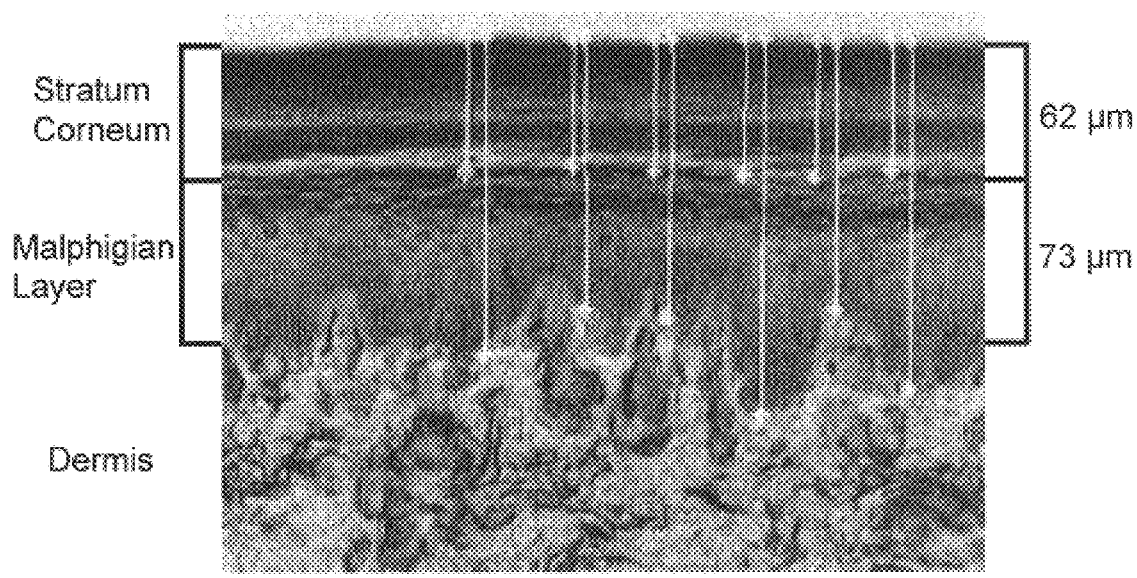
FIG. 4 is a cross-sectional view of a rats' foot skin depicting the distinguishable regions of the skin.
Figure 5:
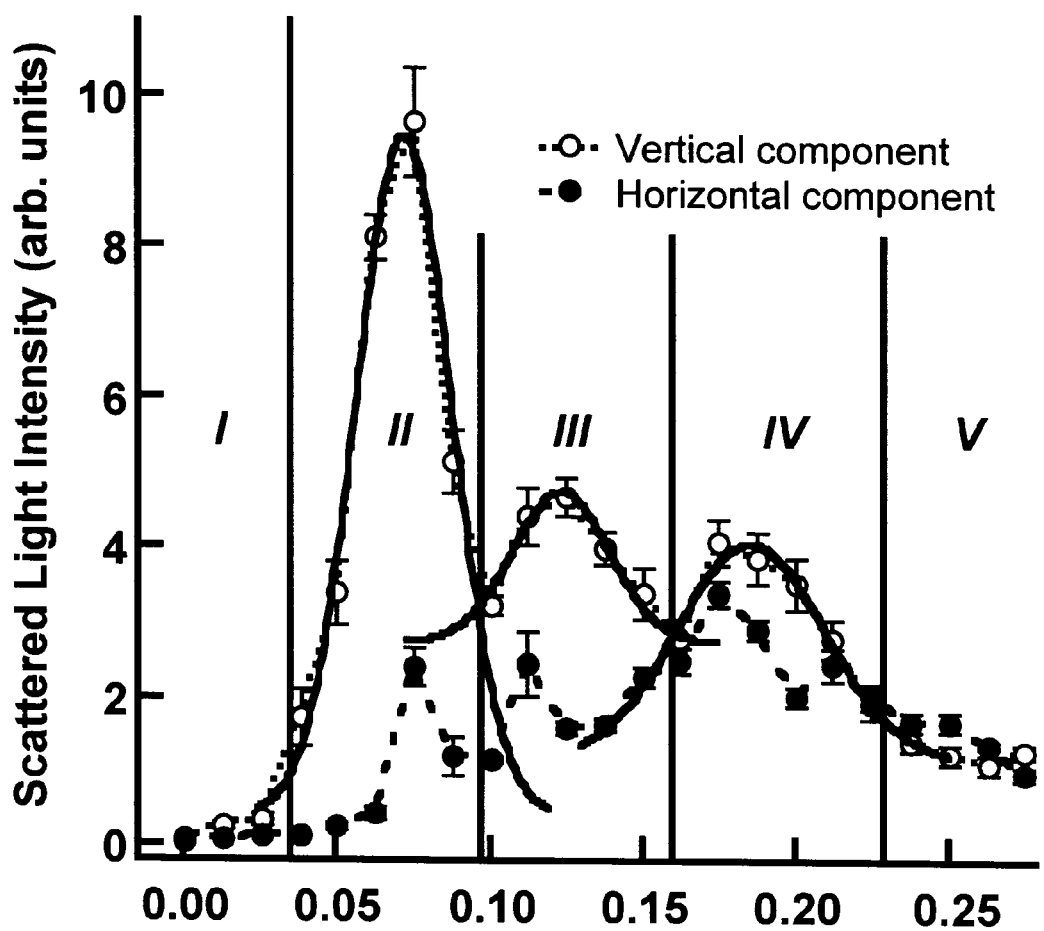
FIG. 5 is a graph representing the observed static intensity properties of back scattered photons emitted at the surface of the tissue collected by optical fiber probe(s) at contiguous locations along the expected path of the initially inserted laser light propagating beneath the skin, as a function of collection polarization and optical fiber position (center-to-center distance is expressed in millimeters)

The algorithm(s) developed for the invention are based on both knowledge of the back scattered light characteristics obtained by the collection optics 5, 6, 7 and 12 as a focused beam of laser light propagates through the skin of a rats' foot under-side whose cross-section is illustrated in FIG. 4, as well as the measurement type desired. Irrespective of measurement type desired or the cost determinant version of the invention utilized, the starting point of the algorithm(s) is the measurement of the static intensity properties of the ∥ and/or ☐ ☐ polarized back scattered laser light emitted at the surface of the skin. FIG. 5 displays the typical results of The focal diameter of the laser light on the skin surface as shown here is ~80 $\mu$m, and the field of view diameter is ~350 $\mu$m. The focal diameter of the polarized laser light expands from ~50 $\mu$m to ~80 $\mu$m due to the multiple scattering of photons within the skin. In addition to beam expansion, multiple scattering also effects changes in the polarization of the incident laser light. Regardless of multiple scattering effects, laser penetration of the tissue is evidenced also by photons emitted at the surface along the expected trajectory of the laser light propagation. The observed image is an electronic reproduction of a photograph taken at 40x magnification. The white circles, later inserted by a computer, represent the different locations from which photons emitted from the surface of the skin are selectively monitored by the translating optical pick-up fiber. At each location, the optical pick-up fiber, covering an area of ~100 $\mu$m$^2$, monitors both the static and dynamic properties of the back scattered laser light. The translated distance between different locations is approximately 0.0125 mm. That is, while maintaining the focal positions of both the incident laser and the microscope objective on the surface the skin, we translated the "pick-up" optical fiber in approximately 0.0125 mm intervals along the microscope objective focal plane following the expected trajectory of the laser beam as it propagates through the sample. The observed behavior of the static and dynamic properties of back scattered light can then be classified into regions, dependent solely upon the location from which photons emitted from the surface of the skin were collected.

With reference now to FIG. 4, there is displayed the static intensity properties of the back scattered photons emitted at the surface of the tissue as a function of translation position and collection polarization. All data were collected using a vertically polarized laser light with an incidence angle $\emptyset_i=60°$, and a 4x microscope objective that collects the back scattered light at a scattering angle $\emptyset_s=120°$. As evidenced, the behavior of the static intensity properties of the back scattered light can be classified into five perceptible regions that are dependent solely on the optical pick-up fiber position and independent of the collection polarization. Differences in the static intensities of polarized and depolarized back scattered light within specific regions are, however, also readily evident due to the effects of multiple scattering of photons. Multiple scattering effects on the back scattered laser light are least observed at the focal point of the incident laser light. That is, the further the laser light propagates through the dense regions of the skin, the more the polarization of the back scattered light is altered due to multiple scattering. Hence, the static behavior of the intensity of back scattered light, by region, can be described as follows:

Region 1. Near the focal point of the incident laser light, but lies in the opposite direction of laser light propagation. For photons to be observed at the surface of this region, they must undergo numerous "collision" events or multiple scattering.

Region 2. The focal point of the incident laser light on the stratum corneum of the skin.

Region 3. The magnitude of polarized and depolarized back scattered laser light intensities observed emanating from the surface to this region are difficult to predict. The initial polarized laser light is expected to reach this region due to forward scattering, which is expected to maintain polarization. The intensity of the initial laser light also should not only diminish exponentially with respect to the depth of propagation, but also due to multiple scattering. Changes in the scattering cross-section of the Malphigian layer had, however, increased the primary contributions to both the polarized and depolarized back scattered light intensities. The magnitude of difference between polarized and depolarized intensities had also diminished, because photons scattered from this region undergo more "collision" events prior to reaching the surface of the tissue.

Region 4. The epidermal/dermal boundary region exhibits a further increase in both the polarized and depolarized back scattered intensities, contrary to the expected steady exponential diminishment of laser light intensity as it propagates further into the tissue. The increase in both the polarized and depolarized back scattered intensities is due not only to changes in the scattering cross-section of the epidermal/dermal boundary, but also due to scattering form the presence of red blood cells. This will become more evident upon comparison with the dynamic properties of the back scattered laser light. Once again, the magnitude of difference between polarized and depolarized intensities had also diminished, because photons scattered from this region undergo further "collision" events prior to reaching the surface of the tissue.

Region 5. Farthest from the initial focal point but along expected trajectory of propagating laser light, propagation. For photons to be observed at the surface of this region, they must undergo numerous "collision" events, as in the case of Region 1. Moreover, the scattering cross-section of the dermis is also weak upon comparison with red blood cells. Thus both the polarized and depolarized back scattered intensities observed at the surface of the tissue diminish somewhat exponentially as the laser light propagates further within this region, as expected. There is also no apparent difference between polarized and depolarized static back scattered light intensities.

As shown, the diameter of the focused laser light on the skin surface is ~80 $\mu$m, and the field of view diameter is ~350 $\mu$m. Clearly visible are the three areas of the skin representing the stratum corneum, Malphigian layer and the dermis. Also to be noted is the highly non-uniform boundary between the epidermal and dermal layers where capillary blood flow is known to occur. As evidenced, the data can be classified into five perceptible regions, dependent solely on the optical position independent of collection polarization. The frequency component of the data representing the average motion of RBC's is noticeably broader than the polarized back scattered light data obtained from the same optical fiber positions. Moreover, the amplitudes of the power spectra obtained from optical fibers positioned in region 2 are noticeably diminished. The frequency component of the data represent the average motion of RBC's over the time course of several heart beats, where RBC's motions are rapid when blood flow is occurring (high frequency) and slow at other times (low frequency). Regardless, the notable features of the averaged spectra are the readily evident differences in the amplitudes and spectral widths of the data with respect to the specific positions of the optical fibers.

Observations of the temporal fluctuations in the scattered light signal yields blood flow and volume characteristics within a specific region of interest. Implicit in all analyses of the temporal fluctuations of scattered light signal is the assumption that the characteristics of blood flow and volume are directly correlated with red blood cell motion and concentration. That is, it is generally considered that the singular difference between the static and dynamic properties of the scattered light signal measured in all studies relating to blood flow is that light scattered by all cells within a specific area contribute to the former, whereas only the motions of red blood cells contribute to changes in the latter. The relative rate of red blood cell (RBC) motions are thus determined by the "frequency" or the "ac" component of the scattered light intensity fluctuations, and their relative concentrations are determined by the magnitude of these fluctuations as well as changes in the static intensity. Several well-known means are available for analysis of the temporal fluctuations in scattered light signal. For the case of monitoring the "real" time characteristics of blood flow, the most frequently used algorithm calculates the changes in the power spectral density, in time. In this particular study, however, we had used two alternate means available for determining the averaged properties of RBC motions, over a period of several heart beats, in order to develop a more thorough understanding of the spectral characteristics of intensity fluctuations within the five perceptible regions of the skin. Based on the results of these studies, we will then describe appropriate algorithms for determining blood flow characteristics, in real time.

FIG. 5 displays the dynamics of the vertically polarized back scattered photons emitted at the surface of the tissue form the five different regions. All data were collected using a vertically polarized laser light with an incidence angle $\emptyset_i=60°$, and a 4× microscope objective that collects the back scattered light at a scattering angle $\emptyset_s=120°$. A simple polarizer in the "vertical" configuration was placed in front of a microscope objective to collect back scattered light of the same polarization as the incident laser light. The polarized back scattered laser thus collected within a small area within each region at the surface of the skin was then "piped" to a photo multiplier tube (see FIG. 2) and converted to an electrical current. This current is next amplified by a factor of ~10$^5$ and forwarded to a high-pass filter with a cut-off frequency at 110 Hz. The photon flux thus represented as voltage is next transferred to a spectrum analyzer which converts temporal fluctuations into a power spectrum in the frequency range of 0–2500 Hz. That is, the spectrum analyzer first digitizes the temporal fluctuations in the back scattered light intensities within a short period of time. It next performs a fast-Fourier transform of the temporal data thereby converting it into the frequency domain. The frequency range of the data corresponds directly to the time period of data collection. The amplitude of the power spectrum is the sum of the squared real and imaginary components of Fourier transform and represents the magnitude of temporal fluctuations. In the current configuration, this process is repeated over a period of 1 to 2 minutes and averaged in order to obtain spectra with good signal-to-noise ratios. Hence the spectra represent the averaged motions of RBC's over the time course of several heart beats, where RBC's motions are rapid when blood flow is occurring and slow at other times. More specifically, the frequency "widths" of the power spectra correspond to the averaged motions of the RBC's. Upon completion of spectrum averages, the data were then transferred to a computer for further analyses.

Figure 6:
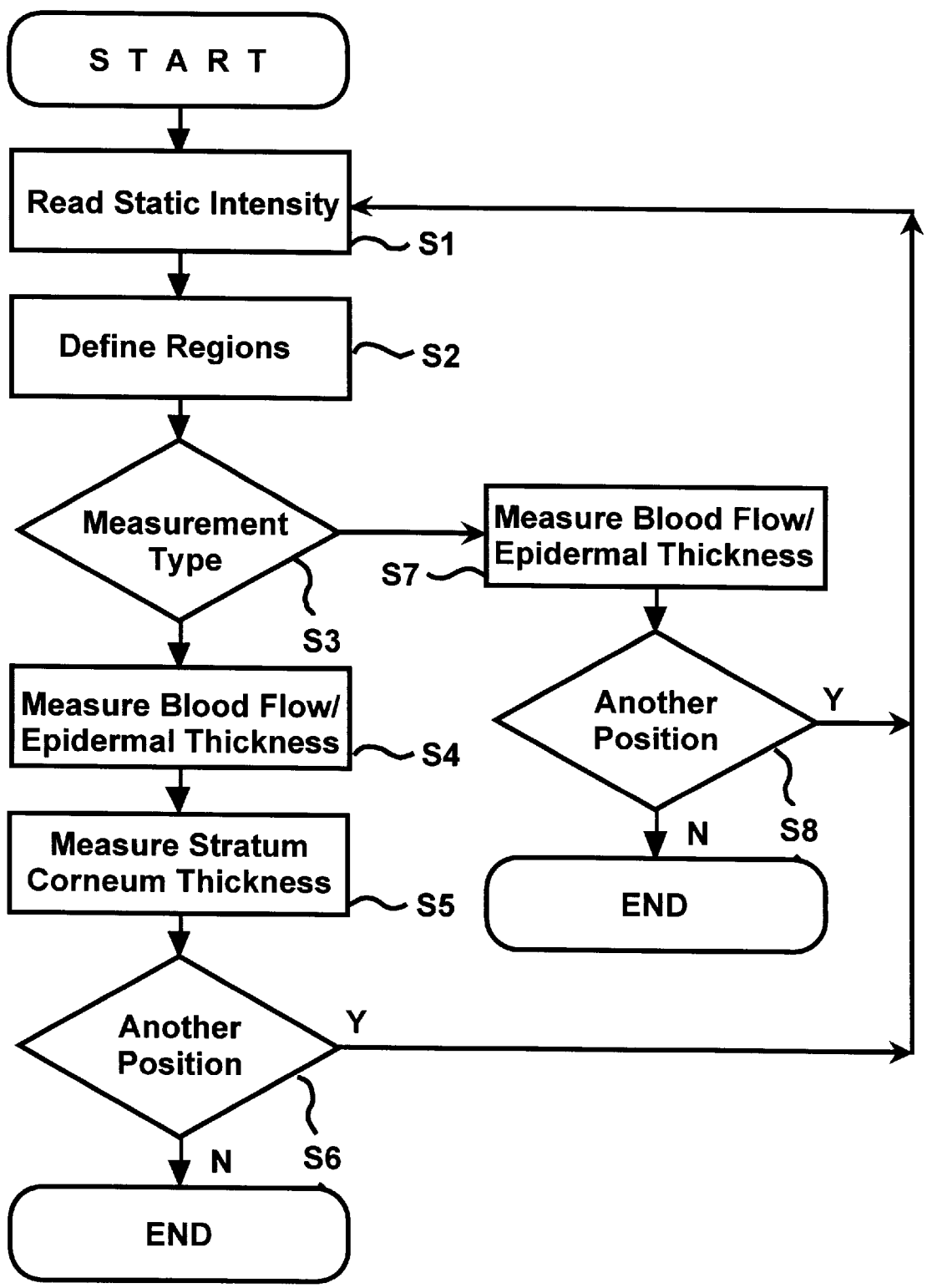
FIG. 6 is a flowchart depicting a method according to the present invention.
Figure 7:
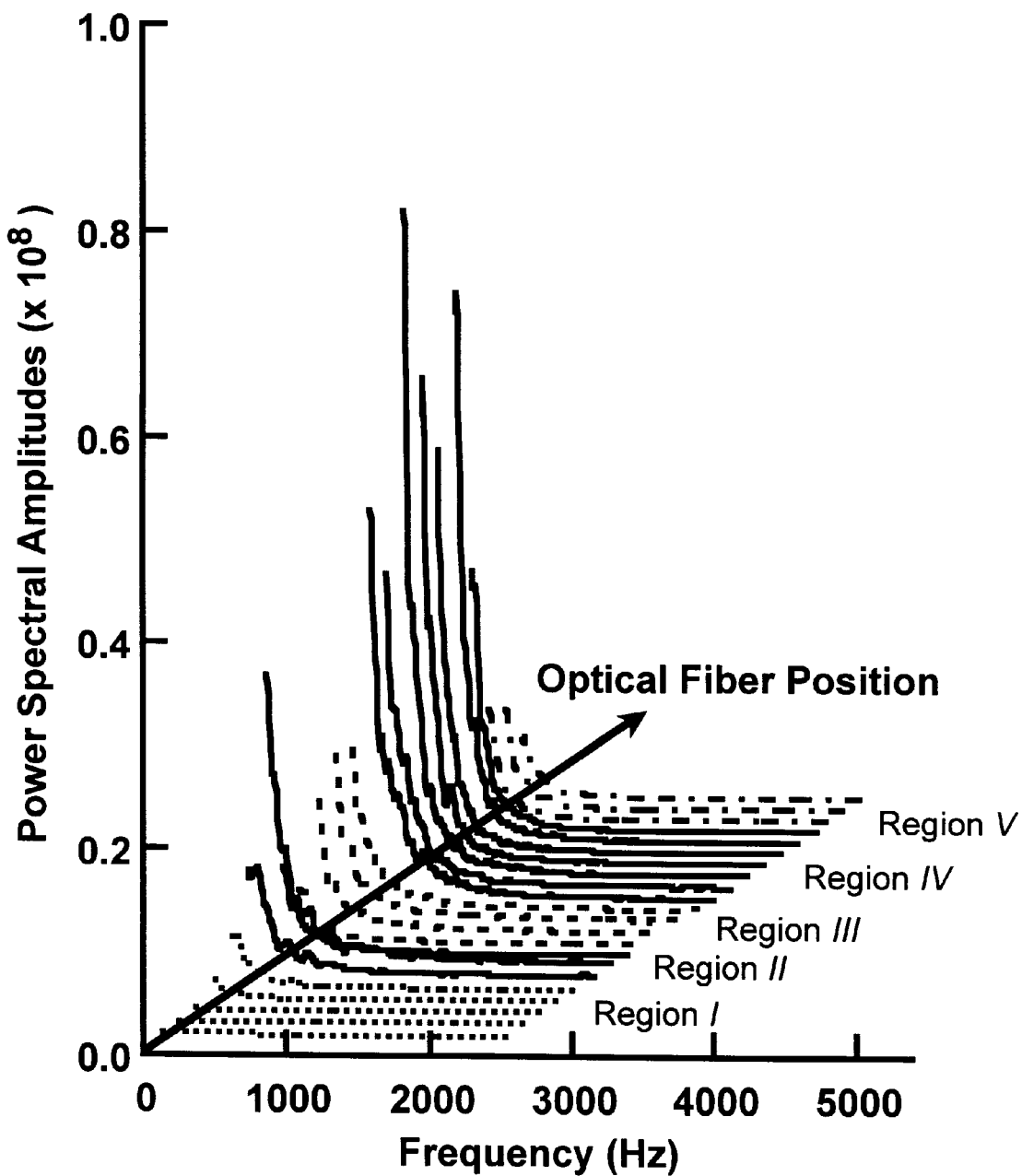
FIG. 7 is a graph of the observed power spectra relating the magnitude of the temporal fluctuations of polarized back scattered laser light, collected by the respective optical fibers probes represented in FIG. 5, as a function of frequency.
Figure 8:
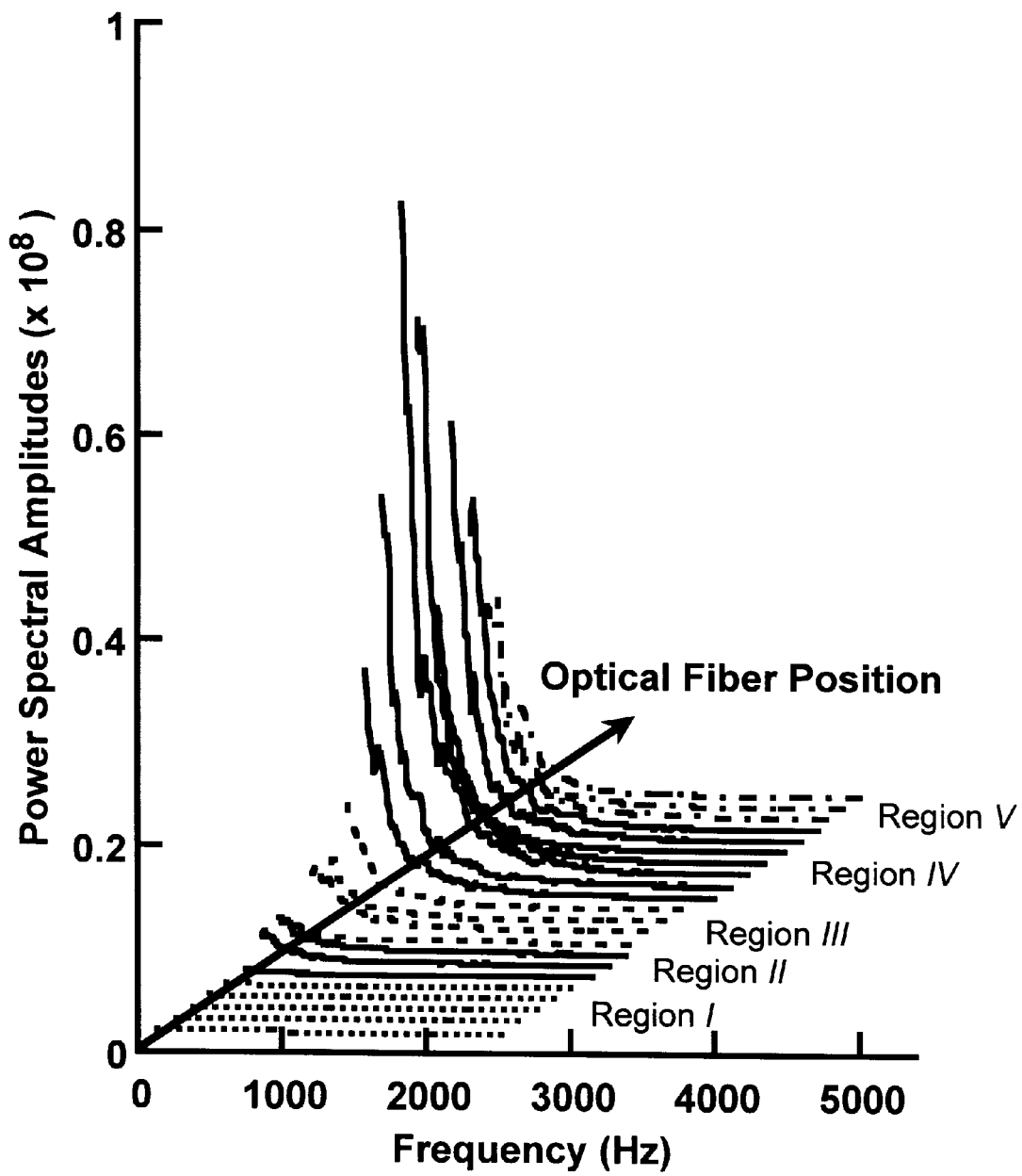
FIG. 8 is a graph of the different behavior of the observed power spectra relating the magnitude of the temporal fluctuations of depolarized back scattered laser light, collected by the respective optical fibers probes represented in FIGS. 5 and 7, as a function of frequency.
Figure 9:
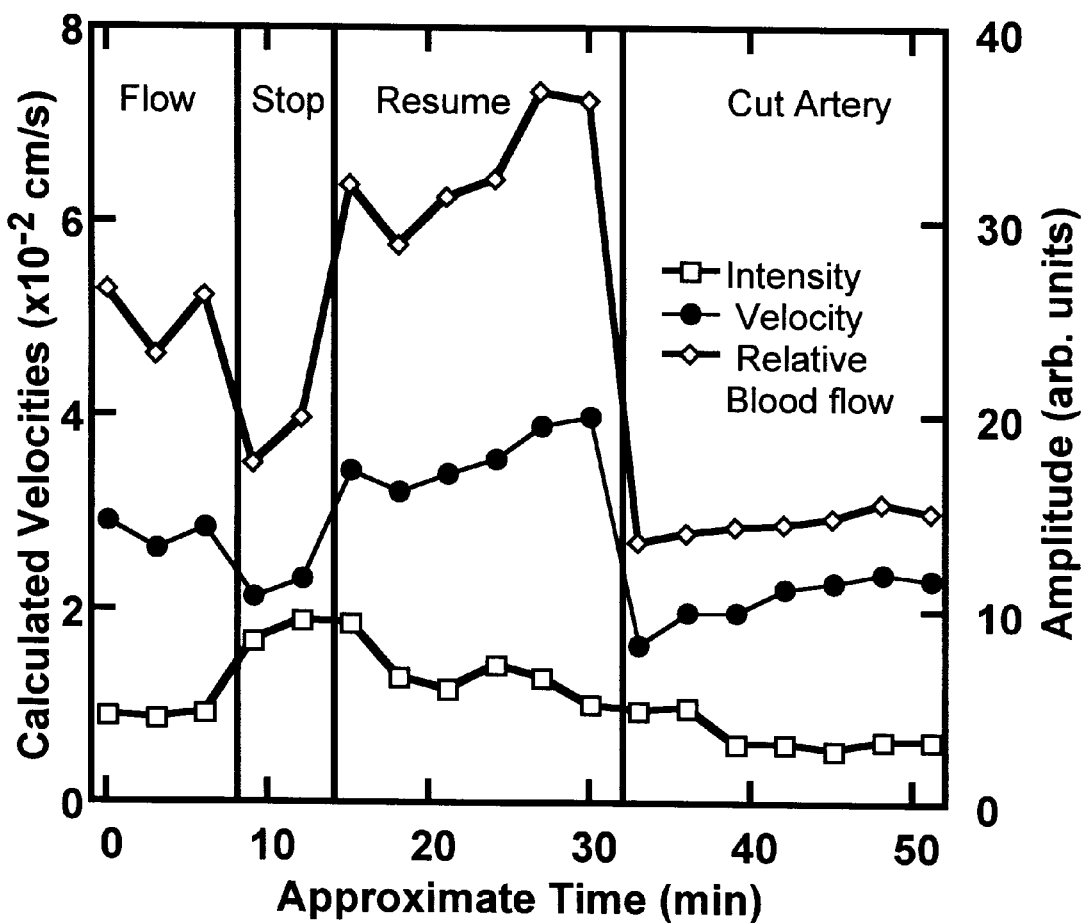
FIG. 9 is a graph showing the changes in the static depolarized back scattered light intensities as well as calculated amplitudes and velocities of power spectra obtained from Region 4, when blood flow under normal circumstances is stopped, allowed to resume and finally when the primary arterial flow is permanently cut-off.
Figure 10:
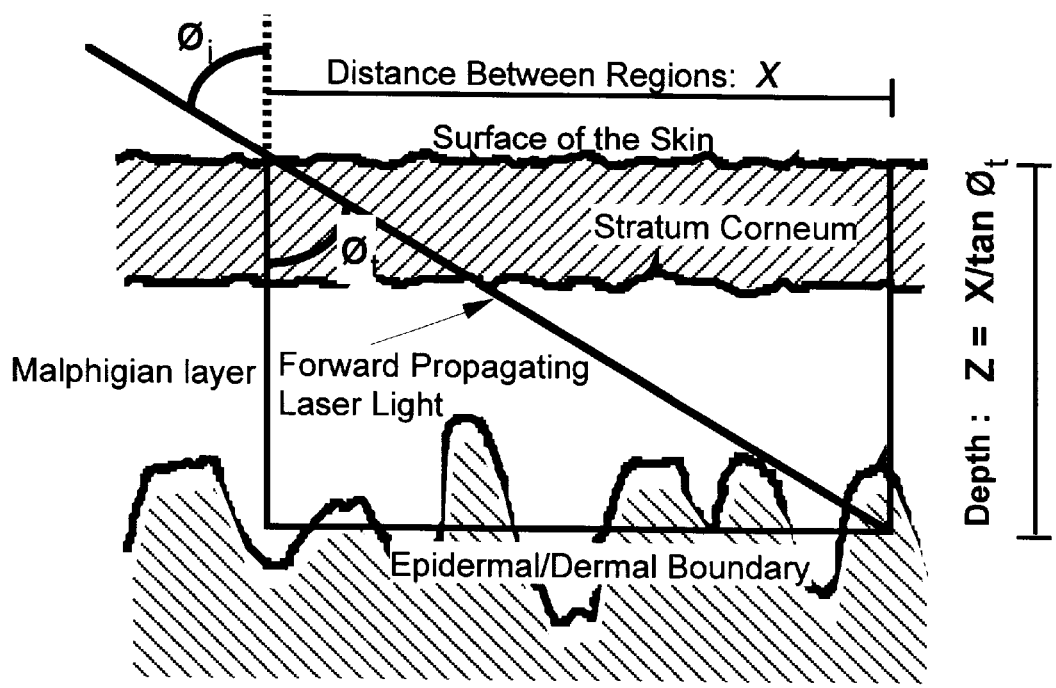
FIG. 10 shows the general principle of the method of triangulation.
Figure 11:
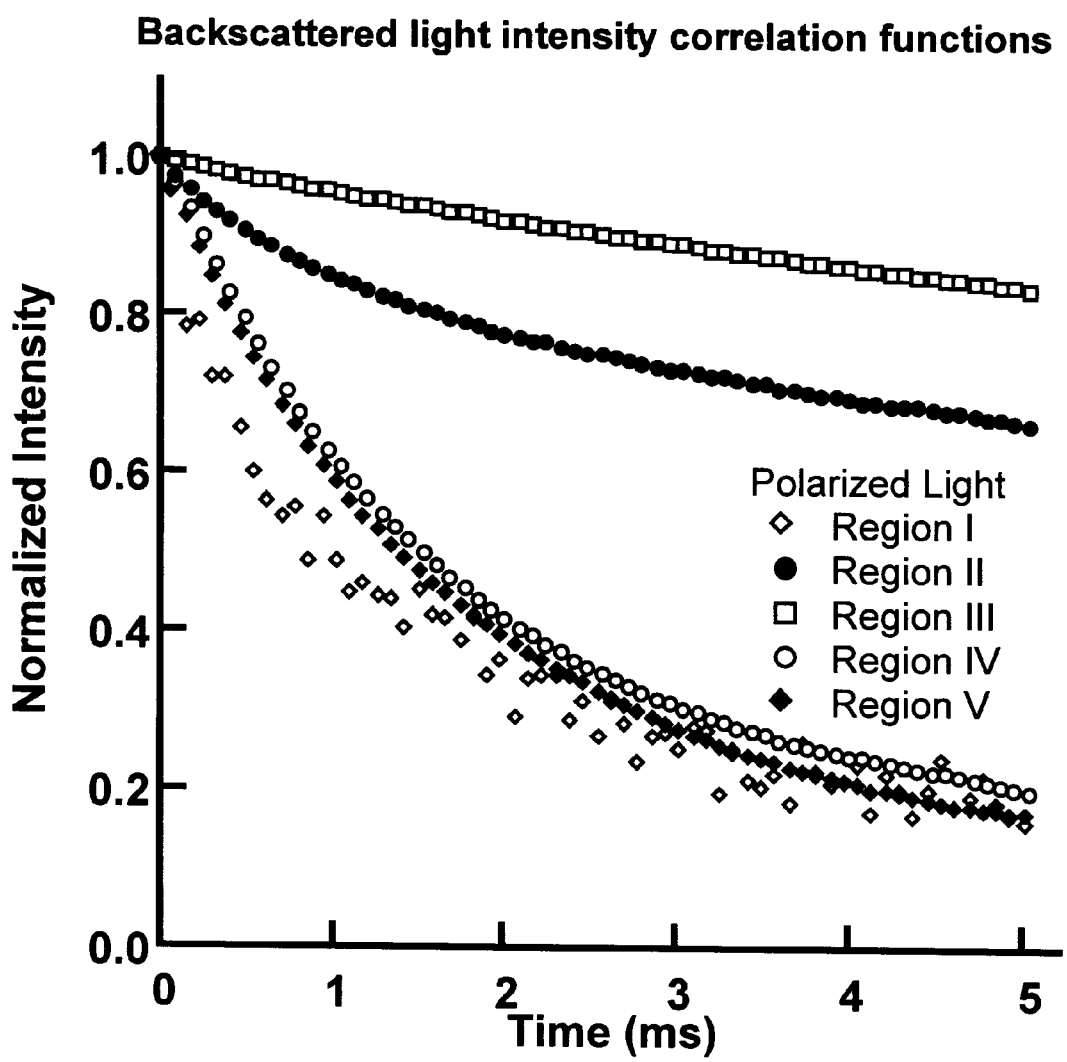
FIG. 11 shows the normalized intensity correlation functions of the polarized back scattered light intensity fluctuations collected at the surface of the skin for the first few series of optical fiber positions.

The method(s) developed for the invention are based on both the knowledge of the back scattered light characteristics obtained by the collection optics and electronics 5, 6, 7, 12, 13, and 14 as a focused beam of laser light propagates through the skin of a rats' foot under-side, whose cross-section is illustrated in FIG. 4, as well as the measurement type desired. Irrespective of measurement type desired or the cost determinant version of the invention utilized, the starting point of the method(s) is the measurement of the ∥ and/or □□ polarized static or time averaged intensity properties of the back scattered laser light emitted at the surface of the skin. FIG. 5 displays the typical results of time averaged sampling 15 of both ∥ and □□ polarized orientations of the intensity of back scattered laser light collected within the field of view of the microscope at each contiguous location on the surface of the skin of a rats' foot under-side. The data were obtained by means of focusing a vertically polarized laser light on the surface of the skin at an incidence angle $\bar{\text{i}}$=60û, and a 4× magnification microscope objective 4 for collecting the back scattered light from the surface of the skin within the field of view of the microscope at a scattering angle $\bar{\text{s}}$=120û. The intial focal diameter of the laser light was ~50 $\mu$m, which had expanded to ~70 $\mu$m on the surface of the skin due to the multiple scattering of photons within the skin. The diameter of the filed of view of the microscope is ~350 $\mu$m. The partitioned area within the field of view of the microscope sampled by optical pick-up fiber(s) 12 after passing through the polarizer 7 is ~100 $\mu$m$^2$, with the center-center distance between different partitions (areas being sampled by an optical pick-up fiber along the expected trajectory of the laser beam beneath the surface of the tissue) being 0.0125 mm. The back scattered light intensty signals thus collected were converted to electrical voltage 13, processed through signal processor which obtains a time average 14, then sent to the voltage read-out 15 for retreival by a computer that displays the data in useful form by the algorithm step S1 illsutrated in schematic form in FIG. 6. The observed behavior of the static intensity properties of back scattered light within each partition/sampling area on the surface of the skin is dependent solely upon the location of the partition or area from where photons were collected, but independent of the or ∥ or □ collection polarization. The observed static intensities for both polarizations are next identified into five perceptible regions in the algorithm step S2. The significant characteristics of the observed static intensity for both ∥ or □ polarized back scattered light from each region are simply defined as follows:

All of the data presented not only in FIG. 5, but also in FIGS. 6,7, 8 & 9 were obtained at essentially the same locality on the rats' foot.

What is claimed is:

1. An apparatus for the non-invasive, in-vivo measurement of blood flow characteristics at precise locations within tissues comprising:

means for illuminating a surface of tissue;

means for collecting back scattered light from said illuminated surface;

means for collecting back scattered light from sub-surface areas of tissue beneath said illuminated surface;

means for producing a visible image from the surface back scattered light and the sub-surface back scattered light; and means for partitioning the back scattered light wherein each partition represents contiguous locations on the surface of the tissue from which the surface emitted back scattered laser light, along a propagating vector or trajectory of the light that initially illuminated the surface of the tissue, is collected such that each partition evidences unique static and dynamic properties of light back scattered from different regions of the tissue through which it traversed at different depths.

2. The apparatus according to claim 1 further comprising a means for producing a visual presentation of the magnitude of blood flow characteristics within the illuminated area of tissue.

3. The apparatus according to claim 2 further comprising a means for determining statiic and dynamic properties of the back scattered light.

4. The apparatus according to claim 3 further comprising a means for determining, the thickness of epidermis tissue, by comparing changes in the static and dynamic properties of back scattered light collected from different regions of tissue and the distance between the different regions.

5. The apparatus according to claim 4 wherein said back scattered light is collected from five different regions of tissue.

6. The apparatus according to claim 4 further comprising a means for determining blood flow at precise depths within said tissue by comparing the static and dynamic properties of the back scattered light.

7. The apparatus according to claim 3 further comprising a means for determining the thickness of stratum corneum tissue, by comparing changes in the static and dynamic properties of back scattered light.

* * * * *